US011287393B2

(12) United States Patent
Stallmann et al.

(10) Patent No.: US 11,287,393 B2
(45) Date of Patent: Mar. 29, 2022

(54) DEEP-FRYING OIL AND/OR DEEP-FRYING FAT SENSOR FOR DETERMINING A DEEP-FRYING OIL AND/OR DEEP-FRYING FAT QUALITY

(71) Applicant: Testo SE & Co. KGaA, Lenzkirch (DE)

(72) Inventors: Siegfried Stallmann, Bonndorf (DE); Markus Munzer, Huffingen (DE); Meinrad Gotz, Bonndorf (DE)

(73) Assignee: Testo SE & Co. KGaA, Lenzkirch (DE)

( * ) Notice: Subject to any disclaimer, the term of this patent is extended or adjusted under 35 U.S.C. 154(b) by 330 days.

(21) Appl. No.: 16/607,408

(22) PCT Filed: Mar. 19, 2018

(86) PCT No.: PCT/EP2018/056856
§ 371 (c)(1),
(2) Date: Oct. 23, 2019

(87) PCT Pub. No.: WO2018/197107
PCT Pub. Date: Nov. 1, 2018

(65) Prior Publication Data
US 2020/0132614 A1      Apr. 30, 2020

(30) Foreign Application Priority Data

Apr. 28, 2017   (DE) .......................... 102017109226.9

(51) Int. Cl.
*G01N 27/22*      (2006.01)
*G01N 33/03*      (2006.01)
*A47J 37/12*      (2006.01)

(52) U.S. Cl.
CPC ........ *G01N 27/221* (2013.01); *A47J 37/1266* (2013.01); *G01N 27/226* (2013.01); *G01N 33/03* (2013.01); *A47J 37/1233* (2013.01)

(58) Field of Classification Search
CPC ........ G01N 27/00; G01N 27/02; G01N 27/06; G01N 27/22; G01N 27/221; G01N 27/226;
(Continued)

(56) References Cited

U.S. PATENT DOCUMENTS 5,056,928 A * 10/1991 Aoki ...................... G01N 11/00
                                                       374/16
5,208,544 A     5/1993 McBrearty et al.
(Continued)

FOREIGN PATENT DOCUMENTS

DE         3201799       8/1983
DE        10155371       5/2003
(Continued)

*Primary Examiner* — Hoai-An D. Nguyen
(74) *Attorney, Agent, or Firm* — Volpe Koenig

(57) ABSTRACT

A frying oil and/or frying fat sensor (1) for determining a frying oil and/or frying fat quality, having a conductor structure (2) that is fixedly connected, at a proximal end, to an electronics part (5), wherein the conductor structure (2) has an inner conductor (6) and an outer conductor (7) that are arranged coaxially with respect to one another and are both connected fixedly to the electronics part at the proximal end. The inner conductor (6), at at least one free end, is guided so as to be able to move relative to the outer conductor (7) in the axial direction in order to compensate temperature-induced mechanical stresses.

15 Claims, 2 Drawing Sheets

(58) Field of Classification Search
CPC ...... G01N 27/228; G01N 27/26; G01N 33/00; G01N 33/02; G01N 33/03; G01N 33/2888; G01N 21/534; A47J 37/00; A47J 37/12; A47J 37/1233; A47J 37/1266; A47J 37/1271; G01R 27/00; G01R 27/02; G01R 27/22; G01R 27/26; G01R 27/2605; A61B 5/0537; G01D 5/00; G01D 5/02; G01D 5/12; G01D 5/14; G01D 5/24; G01D 5/241; G01D 5/2412; G01D 5/2417
USPC ....... 324/600, 649, 658, 663, 664, 684, 685, 324/686, 689, 691, 692, 693, 699
See application file for complete search history.

(56) References Cited

U.S. PATENT DOCUMENTS

| | | | | |
|---|---|---|---|---|
| 5,776,530 | A | * | 7/1998 | Davis .................. A47J 37/1223 426/233 |
| 5,818,731 | A | * | 10/1998 | Mittal .................... G01N 21/59 702/22 |
| 7,030,629 | B1 | * | 4/2006 | Stahlmann ............. G01N 33/26 324/663 |
| 8,497,691 | B2 | * | 7/2013 | Behle .................. G01N 21/534 324/698 |
| 9,510,708 | B2 | * | 12/2016 | Behle ..................... G01N 27/22 |
| 2004/0107957 | A1 | * | 6/2004 | Nishida ............... A47J 37/1266 126/391.1 |
| 2010/0156443 | A1 | | 6/2010 | Nakamura et al. |
| 2015/0057651 | A1 | * | 2/2015 | Bonn ....................... H01Q 1/27 606/33 |
| 2015/0285777 | A1 | * | 10/2015 | Baumann ............... G01N 27/24 73/64.56 |

FOREIGN PATENT DOCUMENTS

| | | |
|---|---|---|
| DE | 4131999 | 8/2003 |
| EP | 2937692 | 10/2015 |
| GB | 2306660 | 5/1997 |
| WO | 9850790 | 11/1998 |

\* cited by examiner

DEEP-FRYING OIL AND/OR DEEP-FRYING FAT SENSOR FOR DETERMINING A DEEP-FRYING OIL AND/OR DEEP-FRYING FAT QUALITY

BACKGROUND

The invention relates to a frying oil and/or frying fat sensor for determining a quality of a frying oil and/or of a frying fat, having a conductor structure, an electronics part arranged on a proximal end of the conductor structure, wherein the conductor structure has an inner conductor and an outer conductor that are arranged coaxially with respect to one another.

Such frying oil and/or frying fat sensors for determining a frying oil and/or frying fat quality are known and are used in order to be able to regularly check the quality of an oil and/or fat used multiple times for frying food. This may be performed for example by way of capacitive sensors, wherein the measured capacitance of the oil and/or fat changes depending on its usage time.

Previously known frying oil and/or frying fat sensors of the type mentioned at the outset however have the disadvantage that the high operating temperature in a bath of oil and/or fat may cause for example an expansion, in particular a change of length, of the various used materials of the conductor electrodes and/or other components. Thus, for example, the inner conductor may change in terms of its position relative to the position of the outer conductor due to temperature-induced mechanical stresses. This results in undesired changes of the distance between the inner and the outer conductor, which changes the capacitance of the measurement capacitor and thus results in serious disruption of a capacitance measurement.

SUMMARY

The invention is therefore based on the object of providing a frying oil and/or frying fat sensor having improved usage properties.

One or more features according to the invention are provided in order to achieve the object. It is in particular provided according to the invention, in order to achieve the object in the case of a frying oil and/or frying fat sensor of the type described at the outset, for the inner conductor to be guided so as to be able to move in the axial direction at at least one of its ends, in particular in order to compensate temperature-induced mechanical stresses. If the high operating temperature in a bath of oil and/or fat, which may sometimes be above 200° C., results in a temperature-induced material change, the length of the inner conductor also changes. By virtue of the movable mounting in the axial direction, the inner conductor is able to expand and/or contract in the axial direction, as a result of which its measurement distance to the outer conductor is not impaired due to temperature-induced mechanical stresses. This makes it possible to avoid serious disruptions when measuring the frying oil and/or frying fat quality by way of a capacitive sensor.

It may be particularly expedient in this case for the inner conductor, at the end guided so as to be able to move in the axial direction, to be guided by a floating support, by way of which this end guided so as to be able to move is supported only radially. A floating support makes it possible for the inner conductor to be guided so as to be able to move axially in both directions, even though no movement of the inner conductor is possible in the radial direction. It is thereby able to be ensured that the diameter of a measurement channel between the inner and outer conductor is constant. As an alternative or in addition thereto, it may therefore be expedient for the inner conductor, at the end guided so as to be able to move, to be guided so as to be able to move relative to the outer conductor.

According to one particularly advantageous configuration, there may be provision for the inner conductor, at its proximal end, to be connected to the electronics part in a positionally fixed manner by way of a fixed support and, at its distal end, to be guided so as to be able to move in the axial direction. This allows a stable construction of the frying oil and/or frying fat sensor, even though tensions of the material are able to be compensated. It may be particularly expedient in this case for the inner conductor to taper to a mandrel in a fixing region of the fixed support and for the inner conductor to be fixedly connected to the electronics part by way of a fixing element via the mandrel. It is thereby possible to design the frying oil and/or frying fat sensor in a particularly stable manner in order to avoid destruction, even in the event of incorrect usage. The frying oil and/or frying fat sensor may thus for example survive being dropped from a table or similar impacts without damage.

As already mentioned previously, it may be particularly advantageous for the frying oil and/or frying fat sensor to be designed as a capacitive sensor, wherein a capacitance, dependent on the quality of the oil and/or fat, between the inner conductor and the outer conductor is able to be measured, wherein the oil and/or fat forms a dielectric whose permittivity is dependent on the usage time of the oil and/or fat. The permittivity or the electricity number $\varepsilon_r$ changes, in particular increases, with increasing usage time, such that it is possible to directly determine the oil and/or fat quality by measuring the capacitance between the inner conductor and the outer conductor.

To be able to allow a measurement of the capacitance that is as accurate as possible and that is also not impacted by larger floating substances and particles in the oil and/or fat, it may be expedient for the frying oil and/or frying fat sensor to have a measurement chamber in which a measurement channel is formed between the outer conductor and the inner conductor, which measurement channel is configured such that, when the frying oil and/or frying fat sensor is put into use, oil and/or fat flows through in the radial and/or axial direction. To be able to avoid depositions inside the measurement channel that have a disadvantageous impact on the measurement, it may be expedient for an inside diameter of the measurement channel, in the inflow direction, to be wider than an inside diameter, running perpendicular to the inflow direction, of the measurement channel. The inflow direction may in this case in particular run perpendicular to the longitudinal axis of the conductor structure. Such a design furthermore has the advantage that many measurements are thereby possible without performing regular servicing since, in contrast to tubular measurement channels, due to the specific geometry of the channel, blockages form less often since the oil and/or fat is able to flow through the measurement channel both in the radial and in the axial direction.

It may be particularly expedient for the measurement chamber to have an inflow opening and an outflow opening, wherein the measurement chamber is configured such that, when the frying oil and/or frying fat sensor is put into use, oil and/or fat flows through the inflow opening into the measurement channel and exits the measurement chamber at the outflow opening. It may furthermore be expedient for at least one inflow opening to the measurement channel and at least one outflow opening out of the measurement channel to be formed on the outer electrode, preferably wherein the inflow openings and/or the outflow openings of the measurement chamber and the outer electrode are aligned flush with respect to one another. It may be particularly advantageous in this case for the inflow opening and/or the outflow opening of the measurement chamber and/or of the outer electrode, which are preferably designed as elongate slots, to extend over an entire length of the outer electrode. It is thereby possible to achieve a particularly homogeneous oil and/or fat flow through the measurement channel in the radial and/or axial direction. To be able to boost a signal strength of the measured signal, there may be provision for the inflow openings and/or the outflow openings of the measurement chamber and/or of the outer electrode to be formed by an elongate slot that extends only over part of the length of the conductor structure and/or of the outer electrode. A signal-to-noise ratio is thereby able to be improved, such that interfering variables have less influence. An elongate slot restricted to a partial length furthermore has the advantage that, during manufacture, less processing time has to be spent on production, as a result of which the manufacturing costs are reduced. The inflow opening and the outflow opening of the measurement chamber and/or of the outer electrode are preferably arranged on different ends of the conductor structure. A compromise would furthermore also be conceivable, in which, rather than an elongate slot, a plurality of individual holes in a series of holes are designed consecutively as inflow opening and/or outflow opening. It is thereby possible to achieve a design of a wall that is as stable as possible and comparatively homogeneous, which improves the measurement quality and at the same time brings about low manufacturing costs for the production thereof.

To avoid an undesired flow of electric current between the inner conductor and the outer conductor, it may be expedient for the frying oil and/or frying fat sensor to have a first insulating element on the distal end of the conductor structure and a second insulating element on the proximal end of the conductor structure, wherein the two insulating elements in each case electrically separate the outer conductor and the inner conductor from one another.

One particularly advantageous configuration may make provision for a or the abovementioned floating support to be formed by a or the abovementioned first insulating element on the distal end of the conductor structure. As an alternative or in addition thereto, it may be particularly expedient for the first insulating element to be fixed on the distal end of the outer conductor. This allows a particularly robust design of the frying oil and/or frying fat sensor.

To be able to guarantee the functional capability of the frying oil and/or frying fat sensor even at high oil and/or fat temperatures, it may be expedient for a or the abovementioned insulating element on the distal end of the conductor structure to be made from plastic or ceramic and/or for the one or the abovementioned second insulating element on the proximal end of the conductor structure to be made from plastic or ceramic.

To be able to improve the robustness of the frying oil and/or frying fat sensor even further, it may be expedient for the outer conductor, by way of its proximal end, to be connected to the electronics part by way of a fixed support.

The invention relates to a frying oil and/or frying fat sensor for determining a frying oil and/or frying fat quality, having a conductor structure that is fixedly connected, at a proximal end, to an electronics part, wherein the conductor structure has an inner conductor and an outer conductor that are arranged coaxially with respect to one another and are both connected fixedly to the electronics part at the proximal end, wherein the inner conductor, at at least one free end, is guided so as to be able to move relative to the outer conductor in the axial direction in order to compensate temperature-induced mechanical stresses.

BRIEF DESCRIPTION OF THE DRAWINGS

The invention will now be described in more detail with reference to exemplary embodiments, without however being limited to said exemplary embodiments. Further exemplary embodiments become apparent from the combination of the features of individual or a plurality of claims with one another and/or with individual or a plurality of features of the exemplary embodiments.

In the Figures.

DETAILED DESCRIPTION

Figure 1:
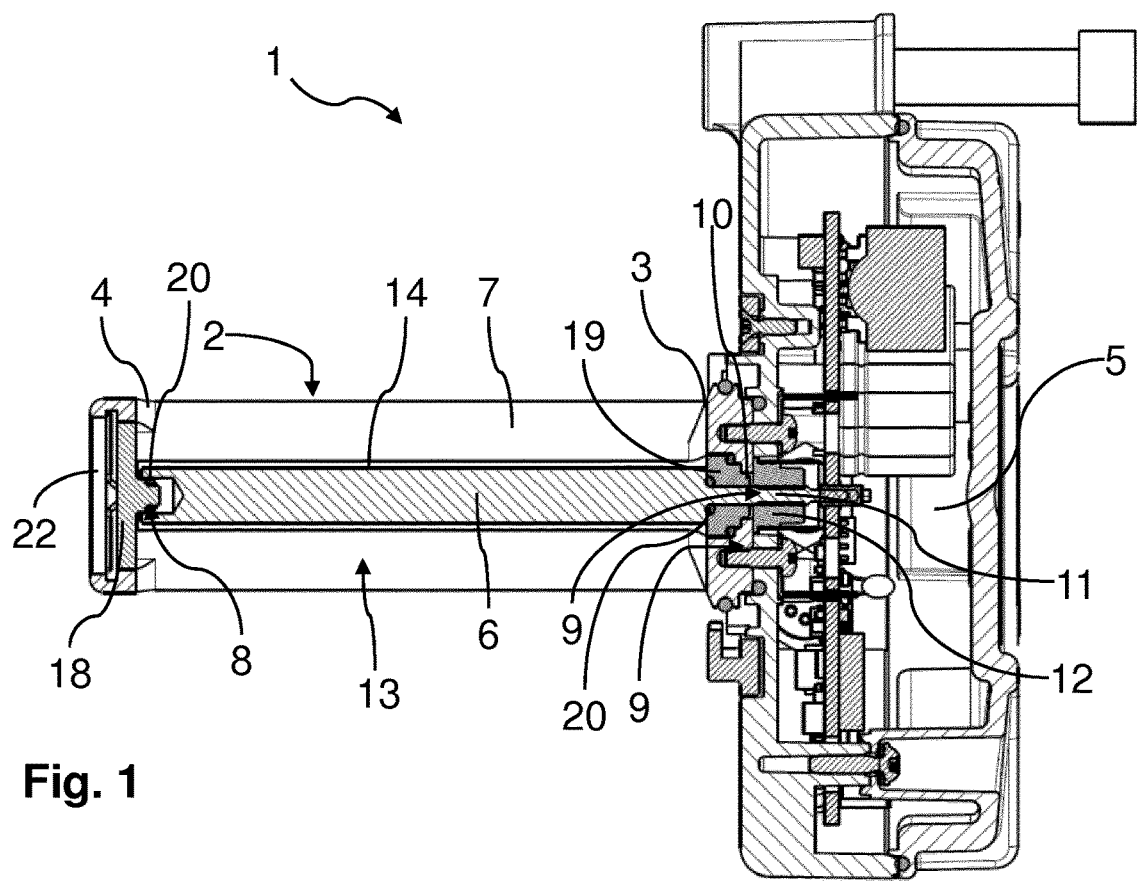
FIG. 1 shows an axial sectional view of one embodiment of the frying oil and/or frying fat sensor.

FIG. 1 shows a frying oil and/or frying fat sensor, referenced in its entirety as 1, for determining a frying oil and/or frying fat quality. The frying oil and/or frying fat sensor 1 has a conductor structure 2, on the proximal end 3 of which an electronics part 5 is arranged.

The conductor structure 2 has an inner conductor 6 and an outer conductor 7, between which an electric field is able to form. The inner conductor 6 and the outer conductor 7 are arranged inside a measurement chamber 13 formed by a housing of the conductor structure 2. A measurement channel 14 of a measurement capacitor whose capacitance is able to be measured is formed between the inner conductor 6 and the outer conductor 7. The inner conductor 6 and the outer conductor 7 are arranged coaxially with respect to one another, wherein a radial distance between the inner conductor 6 and the outer conductor 7 is constant in the measurement channel 14 and/or is the same size over the course of the entire measurement channel 14.

In the capacitive measurement for determining the oil and/or fat quality, the oil and/or fat forms a dielectric whose permittivity $\varepsilon_r$ is dependent on the usage time of the oil and/or of the fat. In this case, the capacitance able to be measured between the inner conductor 6 and the outer conductor 7 changes with increasing usage time, as a result of which it is possible to draw a direct conclusion as to the quality of the oil and/or of the fat.

The inner conductor 6 is guided so as to be able to move in the axial direction on the distal end 4 of the conductor structure 2 in order to be able to compensate temperature-induced mechanical stresses of the conductor material and other components of the frying oil and/or frying fat sensor 1.

A floating support 8 is arranged on the distal end 4 of the conductor structure 2, by way of which floating support a distal end region of the inner conductor 6 is supported only radially, creating only axial mobility of the inner conductor 6. In this case, the inner conductor 6 is also guided so as to be able to move relative to the outer conductor 7 in the axial direction. It is thereby possible to avoid tensions of the inner conductor material caused by temperature-induced material changes, which may lead to the measured capacitance changing even though the quality of the oil and/or of the fat remains the same, since the distance between the capacitor electrodes, that is to say between the inner conductor 6 and the outer conductor 7, changes. As a result, the diameter of the measurement channel 14, even in the case of high temperatures above 200° C., remains constant over the entire length of the measurement channel 14.

Figure 2:
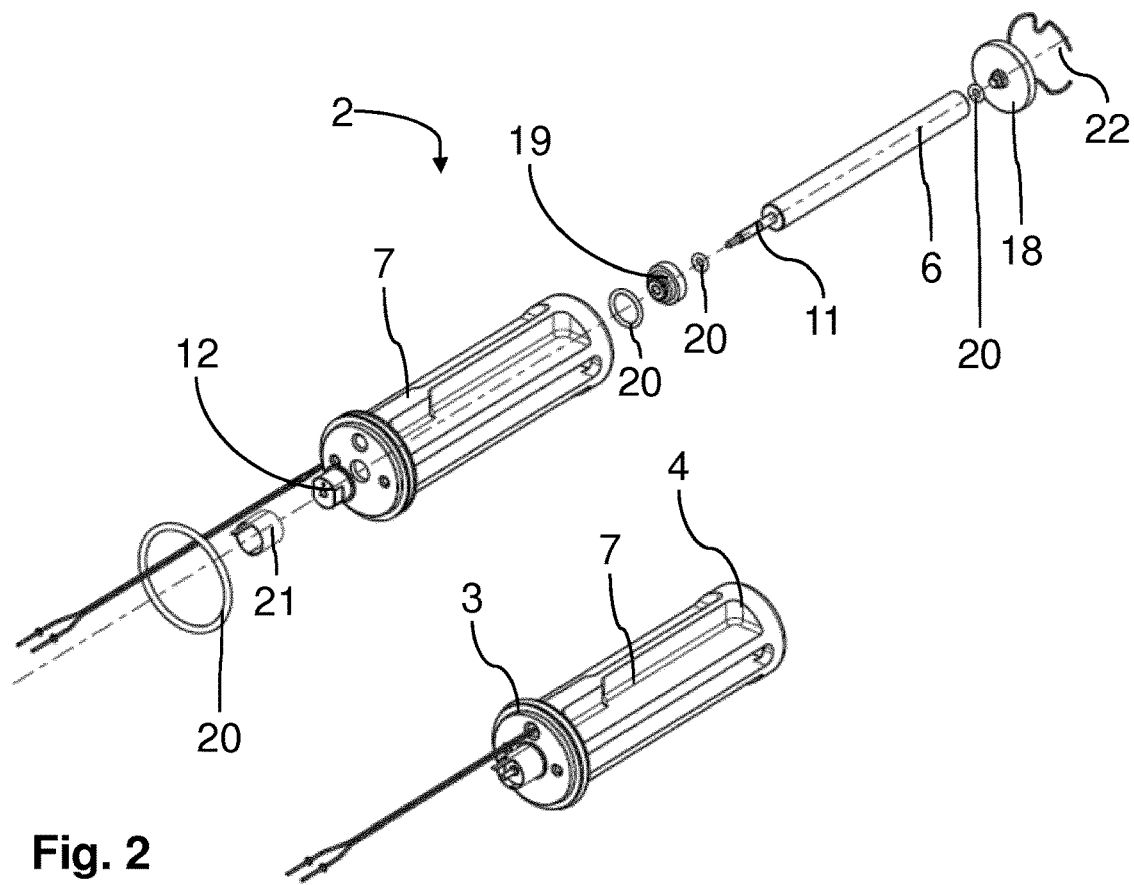
FIG. 2 shows an exploded illustration of the conductor structure of a frying oil and/or frying fat sensor.
Figure 3:
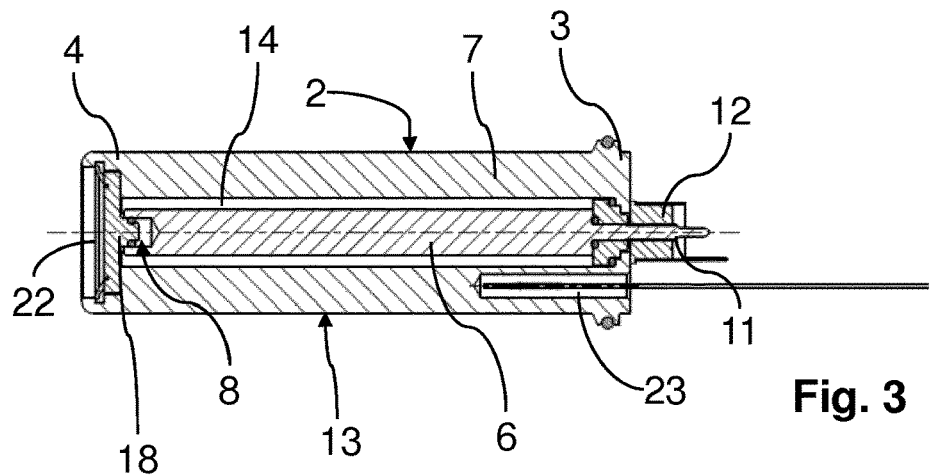
FIG. 3 shows an axial sectional view of the conductor structure from FIG. 2.

FIGS. 2 and 3 illustrate the conductor structure 2 more precisely. As said figures show, the inner conductor 6, at its proximal end, has a tapering region that is designed as a mandrel 11. By way of the mandrel 11, the inner conductor 6 is fixedly connected to the electronics part 5 via a fixing element 12. In this case, the mandrel 11 is inserted into a mandrel receptacle in a fixing region 10 and fixed to the electronics part 5 in a positionally fixed manner by way of the fixing element 12. There may be provision in this case for the mandrel 11 to have an outer thread and for the fixing element 12 to be designed as a nut having a corresponding inner thread. The mandrel 11 is able to be screwed into the fixing element 12 as far as a stop, as a result of which the proximal end of the inner conductor is fixed. The distal part of the inner conductor 6 is in this case still guided so as to be able to move in the axial direction.

As already mentioned above and illustrated in FIGS. 1 and 3, the frying oil and/or frying fat sensor 1 has a measurement chamber 13 in which the inner conductor 6 and the outer conductor 7 are arranged such that a measurement channel 14 is formed between the two of them. When the frying oil and/or frying fat sensor 1 is put into use, oil and/or fat flows from a bath of oil and/or fat through the measurement channel 14 in the radial and axial direction. The oil and/or the fat enters the measurement channel 14 via the inflow opening. An inside diameter of the measurement channel 14 is wider in the inflow direction 15 than an inside diameter, running perpendicular to the inflow direction 15, of the measurement channel 14. The measurement channel 14 may therefore have an elongate, in particular oval or rectangular, cross section. The outer conductor 7 is in this case arranged at least partly concentrically around the inner conductor, wherein the electric field is strongest in the measurement channel 14.

The inner conductor 6 has a round cross section. The outer conductor 7 has a hollow cylindrical cross section, the inner wall of which is arranged at a constant distance from an outer wall of the inner conductor 6.

Figure 4:
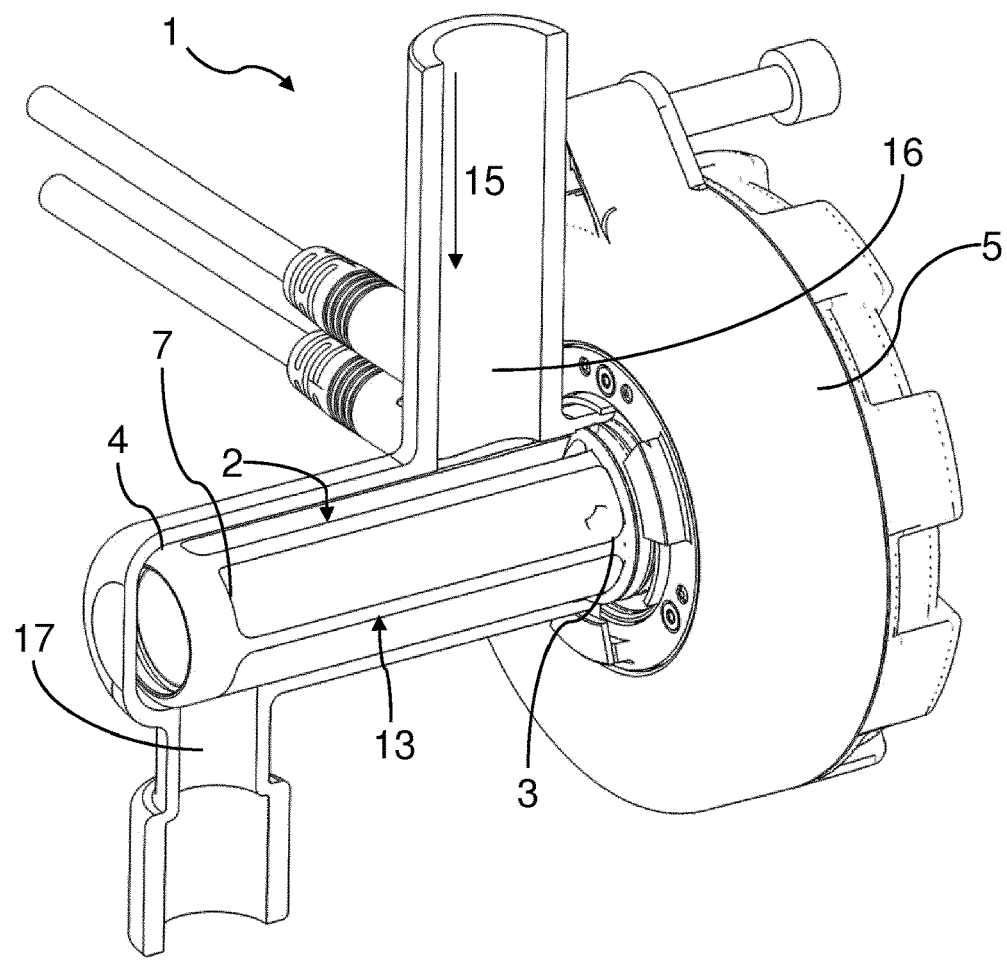
FIG. 4 shows a three-dimensional oblique view of one embodiment of the frying oil and/or frying fat sensor.

FIG. 4 shows that the frying oil and/or frying fat sensor 1 has an inflow opening 16 in which the oil and/or the fat is able to flow into the measurement chamber 13 in the inflow direction 15. The inflow opening 16 is formed by a nozzle that is placed onto the measurement chamber 13 perpendicular to a side wall of the measurement chamber 13. The oil and/or the fat passes into the measurement chamber 13 through a gap in the side wall. The inflow direction 15 of the oil and/or of the fat thus runs perpendicular to the conductor structure 2. When the frying oil and/or frying fat sensor 1 is put into use, the oil and/or the fat therefore flows through the inflow opening 16 into the measurement channel 13, such that a capacitive measurement is possible. The measurement chamber 13 furthermore has an outflow opening 17, via which the oil and/or the fat is able to exit the measurement chamber 13 into the surroundings. The outflow opening 17 is likewise formed by a nozzle that leads into the measurement chamber 13 at a gap in the wall of the measurement chamber 13 and that is aligned perpendicular to the conductor structure 2.

An insulating element 19 is arranged on the proximal end 3 of the conductor structure 2, as illustrated in FIGS. 1 and 3, which insulating element electrically separates the inner conductor 6 and the outer conductor 7 from one another. The insulating element 19 may be made for example from a plastic, in particular a thermoplastic, or from ceramic, in particular glass ceramic. The insulating element 19 is fixedly connected to the outer conductor 7.

A further insulating element 18 is arranged on the distal end 4 of the conductor structure 2, which further insulating element is fixedly connected to the outer conductor 7. The insulating element 18 forms the floating support 8, in which a distal end section of the inner conductor 6 is guided so as to be able to move axially. The insulating element 18 is in this case preferably made from plastic, in particular from a thermoplastic and/or an elastomer. It is furthermore likewise conceivable for the insulating element 18 to be manufactured from ceramic, in particular from glass ceramic.

The electronics part 5 has a connection point, designed as a fixed support 9, for the outer conductor 7. The outer conductor 7 is therefore fixedly connected to the electronics part 5 by way of the fixed support 9.

To screen against interfering electric and/or magnetic fields, the inner conductor 6 and/or its electrical connection line is screened with a screening element 21 in the fixing region 10.

To be able to guarantee better stability of the conductor structure 2, it may be expedient for a securing plate 22 to be arranged on the distal end 4, which securing plate externally closes off the conductor structure 2. The securing plate 22 may preferably have a tool engagement region, as a result of which disassembly is possible. As illustrated in FIG. 2, it may be advantageous, to prevent the oil and/or the fat from penetrating into the electronics part 5, for the individual components of the frying oil and/or frying fat sensor 1 to be sealed off by sealing elements 20. The sealing elements 20 are designed here as O-rings.

The sealing elements 20 create a seal between the second insulating element 19 and the inner conductor 6 that prevents penetration of oil and/or fat into the electronics part 5 via the fixing region 10.

As illustrated in FIG. 3, the frying oil and/or frying fat sensor 1 may have a temperature probe 23. The temperature probe 23 is integrated here into the conductor structure 2. The temperature probe 23 may in particular be integrated into the outer conductor 7. It is possible to measure the temperature of the oil and/or of the fat by way of the temperature probe 23.

LIST OF REFERENCE SIGNS

1 Frying oil and/or frying fat sensor
2 Conductor structure
3 Proximal end of the conductor structure
4 Distal end of the conductor structure
5 Electronics part
6 Inner conductor
7 Outer conductor
8 Floating support
9 Fixed support
10 Fixing region
11 Mandrel
12 Fixing element
13 Measurement chamber
14 Measurement channel
15 Inflow direction
16 Inflow opening 17 Outflow opening
18 First insulating element
19 Second insulating element
20 Sealing element
21 Screening element
22 Securing plate
23 Temperature probe

The invention claimed is:

1. A frying oil and/or frying fat sensor (1) for determining a frying oil and/or frying fat quality, the frying oil and/or frying fat sensor comprising:
   a conductor structure (2) including an inner conductor (6) and an outer conductor (7) that are arranged coaxially with respect to one another,
   an electronics part (5) arranged on a proximal end of the conductor structure (3), and
   the inner conductor (6) is guided so as to be able to move in an axial direction at least at one end thereof to compensate for temperature-induced mechanical stresses.

2. The frying oil and/or frying fat sensor (1) according to claim 1, further comprising a floating support (8), and the inner conductor (6), at the at least one end that is guided for movement in the axial direction, is guided by the floating support (8), which said end being supported only radially.

3. The frying oil and/or frying fat sensor (1) according to claim 1, wherein the inner conductor (6), at a proximal end thereof, is connected to the electronics part (5) in a positionally fixed manner by a fixed support (9) and, at a distal end, is guided for movement in the axial direction.

4. The frying oil and/or frying fat sensor (1) according to claim 1, wherein the frying oil and/or frying fat sensor (1) comprises a capacitive sensor that is configured to measure a capacitance that is dependent on the quality of the oil and/or of the fat, between the inner conductor (6) and the outer conductor (7), wherein the oil and/or the fat is adapted to form a dielectric whose permittivity is dependent on a usage time of the oil and/or of the fat.

5. The frying oil and/or frying fat sensor (1) according to claim 1, further comprising a measurement chamber (13) in which a measurement channel (14) is formed between the outer conductor (7) and the inner conductor (6), said measurement channel is configured such that, when the frying oil and/or frying fat sensor (1) is put into use, the oil and/or fat is adapted to flow through in at least one of a radial or axial direction.

6. The frying oil and/or frying fat sensor (1) according to claim 5, wherein the measurement chamber (13) has an inflow opening (16) and an outflow opening (17), and the measurement chamber (13) is configured such that, when the frying oil and/or frying fat sensor (1) is put into use, the oil and/or fat is adapted to flow through the inflow opening (16) into the measurement channel (14) and exits the measurement chamber (13) at the outflow opening (17).

7. The frying oil and/or frying fat sensor (1) according to claim 1, further comprising a first insulating element (18) on a distal end of the conductor structure (4) and a second insulating element (19) on a proximal end of the conductor structure (3) that electrically separate the outer conductor (7) and the inner conductor (6) from one another.

8. The frying oil and/or frying fat sensor (1) according to claim 7, further comprising a floating support (8) formed by the first insulating element (18) on the distal end of the conductor structure (4).

9. The frying oil and/or frying fat sensor (1) according to claim 7, wherein the first insulating element on the distal end of the conductor structure (4) is made from plastic or ceramic.

10. The frying oil and/or frying fat sensor (1) according to claim 1, wherein a proximal end of the outer conductor (7), is fixedly connected to the electronics part (5) by of a fixed support (9).

11. The frying oil and/or frying fat sensor (1) according to claim 1, wherein the inner conductor (6), at the at least one end that is guided, is guided for movement relative to the outer conductor (7).

12. The frying oil and/or frying fat sensor (1) according to claim 3, wherein the inner conductor (6) tapers to a mandrel (11) in a fixing region (10) of the fixed support (9) and the inner conductor (6) is fixedly connected to the electronics part (5) by a fixing element (12) via the mandrel (11).

13. The frying oil and/or frying fat sensor (1) according to claim 5, wherein an inside diameter of the measurement channel (14), in an inflow direction (15), is wider than an inside diameter, running perpendicular to the inflow direction (15), of the measurement channel (14).

14. The frying oil and/or frying fat sensor (1) according to claim 7, wherein the first insulating element is fixed on the distal end of the outer conductor (7).

15. The frying oil and/or frying fat sensor (1) according to claim 7, wherein the second insulating element on the proximal end of the conductor structure (3) is made from plastic or ceramic.

* * * * *